US006626827B1

United States Patent
Felix et al.

(10) Patent No.: US 6,626,827 B1
(45) Date of Patent: Sep. 30, 2003

(54) FLUID MANAGEMENT ASSEMBLY FOR USE IN ENDOSCOPIC PROCEDURES

(75) Inventors: Augustus Felix, Cranston, RI (US); Debra Ranucci, Smithfield, RI (US)

(73) Assignee: C. R. Bard, Inc., Murray Hill, NJ (US)

( * ) Notice: Subject to any disclaimer, the term of this patent is extended or adjusted under 35 U.S.C. 154(b) by 384 days.

(21) Appl. No.: 09/654,786

(22) Filed: Sep. 1, 2000

(51) Int. Cl.[7] .................................................. A61B 1/12
(52) U.S. Cl. ...................... 600/156; 600/573; 600/581; 600/578; 600/158; 600/153; 604/317; 604/118; 604/119; 604/319; 604/327
(58) Field of Search ................................. 600/156, 573, 600/158, 153, 574, 578, 581, 582; 604/317, 327, 319, 328, 322, 329, 330, 118, 119

(56) References Cited

U.S. PATENT DOCUMENTS

| | | | |
|---|---|---|---|
| 3,626,928 A | | 12/1971 | Barringer .................... 128/2 R |
| 3,885,565 A | * | 5/1975 | Satchell ...................... 128/276 |
| 4,072,153 A | * | 2/1978 | Swartz ................... 128/350 R |
| 4,598,458 A | * | 7/1986 | McAllester ............. 128/132 D |
| 4,643,197 A | * | 2/1987 | Greene et al. .............. 128/762 |
| 4,662,871 A | * | 5/1987 | Rafelson ..................... 604/119 |
| 4,836,189 A | * | 6/1989 | Allred, III et al. .............. 128/6 |
| 4,856,527 A | * | 8/1989 | Karcher et al. ............. 128/634 |
| 5,030,202 A | | 7/1991 | Harris .......................... 604/27 |
| 5,108,366 A | | 4/1992 | Schatz .......................... 604/55 |
| 5,116,327 A | | 5/1992 | Seder et al. ................. 604/284 |
| 5,395,354 A | * | 3/1995 | Vancaillie ................... 604/314 |
| 5,437,629 A | | 8/1995 | Goldrath ...................... 604/21 |
| 5,547,456 A | * | 8/1996 | Strobl et al. ................ 600/133 |
| 5,599,333 A | | 2/1997 | Atkinson .................... 604/326 |
| 5,720,299 A | * | 2/1998 | Theodoru ................... 128/760 |
| 5,738,656 A | | 4/1998 | Wagner ...................... 604/119 |
| 5,814,009 A | | 9/1998 | Wheatman .................... 604/21 |
| 5,827,229 A | * | 10/1998 | Auth et al. .................. 604/171 |
| 5,840,077 A | | 11/1998 | Rowden et al. ............. 606/112 |
| 5,855,549 A | | 1/1999 | Newman .................... 600/135 |
| 5,928,249 A | | 7/1999 | Saadat et al. ............... 606/119 |
| 6,070,586 A | | 6/2000 | Harroll et al. .............. 128/849 |
| 6,071,267 A | | 6/2000 | Zamierowski .............. 604/289 |
| 6,149,633 A | * | 11/2000 | Maaskamp .................. 604/137 |
| 6,159,160 A | * | 12/2000 | Hsei et al. .................. 600/560 |
| 6,213,124 B1 | * | 4/2001 | Butterworth ................ 128/853 |
| 6,213,970 B1 | * | 4/2001 | Nelson et al. ................ 604/35 |

OTHER PUBLICATIONS

Instructions for Use—Hydroflex™–Hysteroscopic Distention Tubing Set.

* cited by examiner

Primary Examiner—Ira S. Lazarus
Assistant Examiner—Tu Cam Nguyen
(74) Attorney, Agent, or Firm—Darby & Darby

(57) ABSTRACT

A fluid management assembly for use in an endoscopic procedure is provided. The assembly comprises a first line for fluid to flow therethrough from an endoscope to a Y-connector and a second line for fluid to flow therethrough from a drape to the Y-connector. The Y-connector is also in fluid communication with a third line which connects the Y-connector to a suction source which supplies a suction force and receives the fluid. According to the present invention the Y-connector is located in close proximate relation with respect to the suction source and the first and second lines are preferably co-joined along a portion of their lengths. The first and second lines define scope and drape legs, respectively, which are elongated in comparison to more conventional designs. These features of the present invention serve to optimize distention and eliminate pressure fluctuations in the operative organ during the surgical procedure.

20 Claims, 2 Drawing Sheets

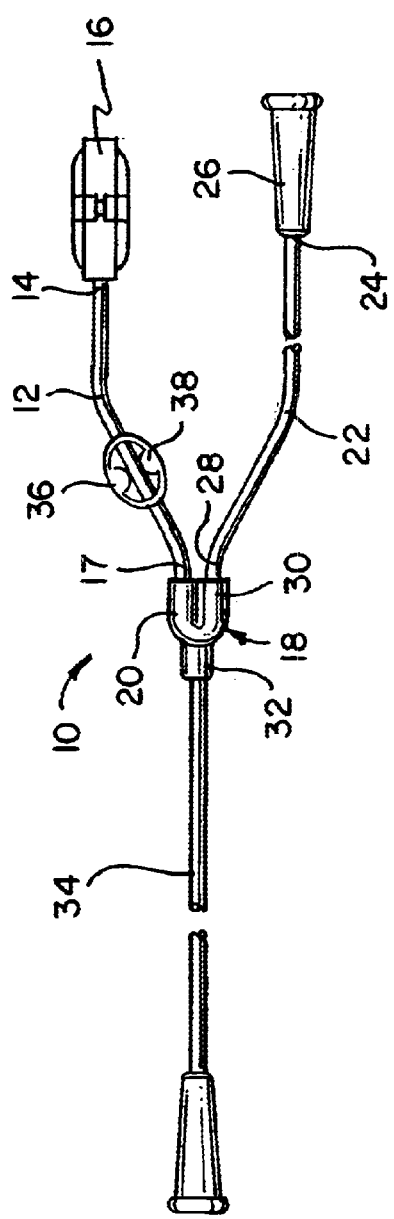
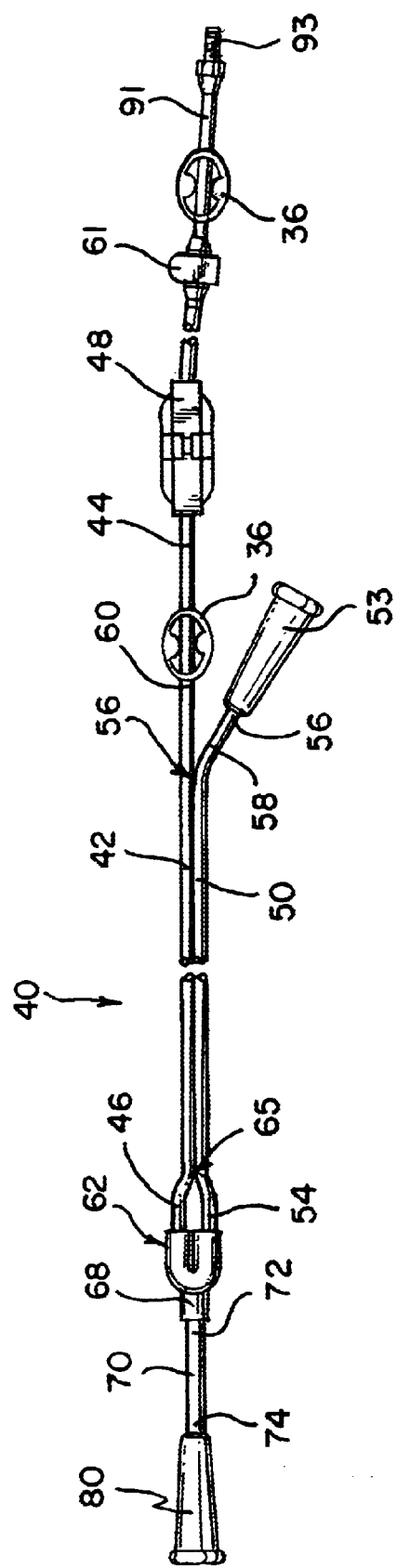

FLUID MANAGEMENT ASSEMBLY FOR USE IN ENDOSCOPIC PROCEDURES

FIELD OF THE INVENTION

The invention relates to the field of fluid management systems and, more particularly, to an endoscope distention fluid management assembly for use in an endoscopic operative procedure, such as a hysterectomy procedure.

BACKGROUND OF THE INVENTION

The occurrence of surgical procedures which require medical instruments which use fluid irrigation to ensure visualization of the operative area continues to increase over time. One such medical procedure is a hysteroscopic procedure in which a hysteroscope is used to provide fluid irrigation for permitting visualization of the uterine area. Operative hysteroscopy uses pressurized solutions to distend the operative space (the uterus) so that the clinician can clearly identify the anatomy and subsequently remove the diseased tissue during the operative procedure. Over the duration of the surgical procedure, an individual, such as a nurse, measures the amount of fluid being delivered to the patient and the amount of fluid which is recovered from the patient during the procedure. If the amount of fluid being recovered from the patient is less than the amount of fluid being delivered to the patient, a fluid deficit results.

A fluid deficit may result due to any number of reasons including but not limited to the occurrence of fluid loss which results from leakage through a cervical seal as well as fluid loss through an outflow port of the hysteroscope. Since fluid monitoring is a very important part of managing the patient during the operative procedure, all fluids exiting the uterus must be balanced with the fluids entering the organ so as to maintain an account of the occurrence of any fluid deficit during the procedure. In addition, it is important to monitor whether a fluid imbalance occurs as a result of the patient absorbing an excessive quantity of fluid. If a patient absorbs an excessive quantity of fluid, complications can result including those of a serious nature. Therefore, it is important to continuously monitor the fluids in the operative space during the operative procedure to ensure that the uterus is properly distended to permit sufficient visualization thereof and to ensure that the patient's health is not jeopardized.

Typically, the clinician will use a fluid collection system as the surgical procedure is being performed so that fluid may be recovered and collected from the operative site. As previously mentioned, the endoscope contains an outflow port in which fluid is transferred from the uterus to a remote location where it is collected in a receptacle and then measured to ascertain the total fluid loss of the patient during the procedure. During the procedure, a hysteroscopy pouch drape or the like is typically used and is disposed underneath the patient's buttocks area. This drape is designed to collect any fluid which may be discharged from the uterus during the procedure. The fluid is caught in a pouch portion and is collected therein for delivery to the remote collection receptacle. The drape and more specifically the pouch portion thereof is also likewise connected to the collection receptacle by means of a fluid carrying device such as attachable tubing which permits the fluid to be effectively transferred to the collection receptacle.

Now referring to FIG. 1 which illustrates a conventional fluid management assembly, generally designated at 10. The collection system 10 comprises a first fluid carrying member 12 which is connected at a first end 14 to a first connector 16 which is designed to engagingly mate with the outflow port of the hysteroscope (not shown). A second end 17 of the first fluid carrying member 12 is connected to a Y-connector 18 and more specifically is connected to a first leg 20 thereof. The management assembly 10 further includes a second fluid carrying member 22 which is coupled to the hysteroscopy pouch drape (not shown) at a first end 24 thereof. The first end 24 preferably has a second connector 26 coupled thereto which is designed to permit attachment of the second fluid carrying member 22 to the hysteroscopy pouch drape. A second end 28 of the second fluid carrying member 22 is connected to a second leg 30 of the Y-connector 18 with the first and second legs 20, 30 being in parallel orientation relative to one another.

The Y-connector 18 also includes a main leg 32 which extends in an opposite direction relative to the first and second legs 20, 30. The main leg 32 receives and is coupled to a main fluid carrying member 34 which receives fluid from both the first and second fluid carrying members 12, 22 and directs the fluid to a suction source (not shown). It will be appreciated that the suction source serves to supply a sufficient suction force so that the fluid is drawn through all the members 12, 22, 34 and is delivered to the collection receptacle (the suction source). Preferably, the first, second, and third fluid carrying members 12, 22, 34, respectively, comprise tubing which is suitable for use in the intended medical procedures described herein. At the end of the procedure, the total volume of the fluid collected in the collection receptacle is reconciled with the total input volume and a fluid deficit, if any, is calculated for the patient.

The management assembly 10 also preferably includes a pinch clamp 36 which is disposed about the first fluid carrying member 12 and is designed to selectively restrict the flow rate of fluid through the first carrying member 12. The illustrated pinch clamp 36 includes a ratchet mechanism which is designed to pinch the first fluid carrying member 12 between a pair of protuberances, generally indicated at 38. As the pinch clamp 36 is manipulated so that the first fluid carrying member 12 is further constricted between the protuberances 38, the flow rate of the fluid decreases.

The management assembly 10 also preferably further includes a flow restrictor (not shown) which is coupled to the first end 24 of the second fluid carrying member 22. The hysteroscopy pouch drape does not always contain fluid and when this condition exists, the Y-connector 18 is vented to atmosphere which reduces the suction applied to the endoscope line (the first fluid carrying member 12). By being inserted into the second fluid carrying member 22, the flow restrictor 39 is designed to enhance the suction in the endoscope line so that the fluid is properly drawn from the hysteroscope whether or not fluid is present in the drape.

While suitable for its intended purpose, the above-described conventional management assembly 10 has associated disadvantages which result in reduced uterine distention. Because uterine distention is dependent upon on both inflow and outflow performance, optimization of the fluid inflow and outflow will result in uterine distention being likewise optimized. During distention of the uterus, fluid is pumped into the uterine space to develop positive pressure which is required in order to increase the volume of the uterine space. The fluid pumped into the uterine space is delivered by means of the hysteroscope which has an inflow port along with the aforementioned outflow port. Fluid which enters the uterine space through the inflow port is then relieved through the outflow port. When the fluid is relieved through the outflow port, it is permitted to flow under gravity into the hysteroscopy pouch drape for subsequent aspiration into the collection receptacle.

During gravity flow from the outflow port, the fluid flows through a vertical length of the first fluid carrying member 12 which creates a siphon effect. The magnitude of the siphon effect will depend upon the length of the first fluid carrying member 12 which hangs below the uterus of the patient. This siphon effect acts as a negative pressure which serves to reduce the positive pressure acting within the uterine cavity and hence, reduces the amount of uterine distention. This reduction in distention, if significant enough, can slow down the surgical procedure and result in an increase in bleeding which in turn results in a reduction in visibility of the anatomy.

Another associated disadvantage of the conventional system is that often suction is applied directly to the outflow port of the hysteroscope and during this type of application high levels of suction may be applied to the uterus and hence reduce the distention thereof. This results in the same above-mentioned difficulties being experienced and generally complicates the surgical procedure. In addition, the Y-connector 18, as previously described, serves to receive both the fluids from the first and second fluid carrying members 12, 22 under suction so that all of the patient's fluids may be pooled into one collection canister (the collection receptacle). Using a Y-connector arrangement can result in a decrease in performance since the system flow needs to be mechanically balanced to allow adequate simultaneous entrainment from both the first and second legs 20, 30 of the Y-connector 18. If the first and second legs 20, 30 are not balanced, flow may be biased to one of the first and second legs 20, 30 because the fluid seals the leg with less resistance causing a sumping action to occur. The occurrence of a sumping action results in cycling of intrauterine pressures, uterine bleeding and increases surgical procedure time. For example, when there is a fluid build-up in the hysteroscopy pouch drape, the drape acts as a reservoir creating a column of fluid in the second fluid carrying member 22. Because of the column of fluid, the pressure in the second fluid carrying member 22 is increased and this may create a fluid seal which limits the fluid flow through the first fluid carrying member 12 (endoscope line). This causes a recycling of the intrauterine pressure which is undesirable.

Therefore, there is need for an improved management assembly for use in an endoscopic, e.g., hysteroscopic, surgical procedure which permits the operative organ to be optimally distended during the entire surgical procedure. The management assembly of the present invention satisfies these and other needs.

SUMMARY OF THE INVENTION

The present invention concerns improvements in fluid management assemblies for use in endoscopic procedures. According to the present invention, it has been discovered that locating the Y-connector so as to elongate the scope and drape legs results in improved distention and eliminates the deficiencies associated with the conventional designs. Specifically, the Y-connector is positioned so that the Y-connector is in proximate relationship with the suction canister which provides suction forces and collects the fluid. Because the Y-connector is proximately located relative to the suction source, the Y-connector is exposed to a greater suction force. Furthermore, the elongation of the scope and drape legs of the present assembly results in minimal mixing of the fluids and minimizes the dependency between the lines. By delivering the fluids further downstream before they are combined at the Y-connector and by subjecting the Y-connector to a greater suction force, pooling of fluid within the Y-connector is avoided. As will be described in greater detail hereinafter, the position of the Y-connector eliminates pooling since the fluid is entrained upwardly into the Y-connector in comparison with the conventional design in which the fluid is entrained downwardly. The present assembly also eliminates or substantially reduces the likelihood that a liquid seal will occur in the Y-connector resulting in flow restriction within the endoscopic line because the present design permits the pressure within the endoscopic and drape lines to be substantially balanced.

The arrangement of the Y-connector relative to the scope and drape legs also eliminates the need for a flow restrictor in the drape line yet provides adequate suction on the endoscope when the drape is empty. Accordingly, any pressure fluctuations in the uterus are eliminated and flow is enhanced when fluid is aspirated simultaneously from the drape and the scope.

Other features and advantages of the present invention will be apparent from the following detailed description when read in conjunction with the accompanying drawings.

BRIEF DESCRIPTION OF THE DRAWINGS

FIG. 1 is a side elevational view of a conventional fluid management assembly for use during an hysteroscopic surgical procedure;

FIG. 2 is a side elevational view of a fluid management assembly according to an exemplary embodiment of the present invention.

DETAILED DESCRIPTION OF THE PREFERRED EMBODIMENTS

Figure 3:
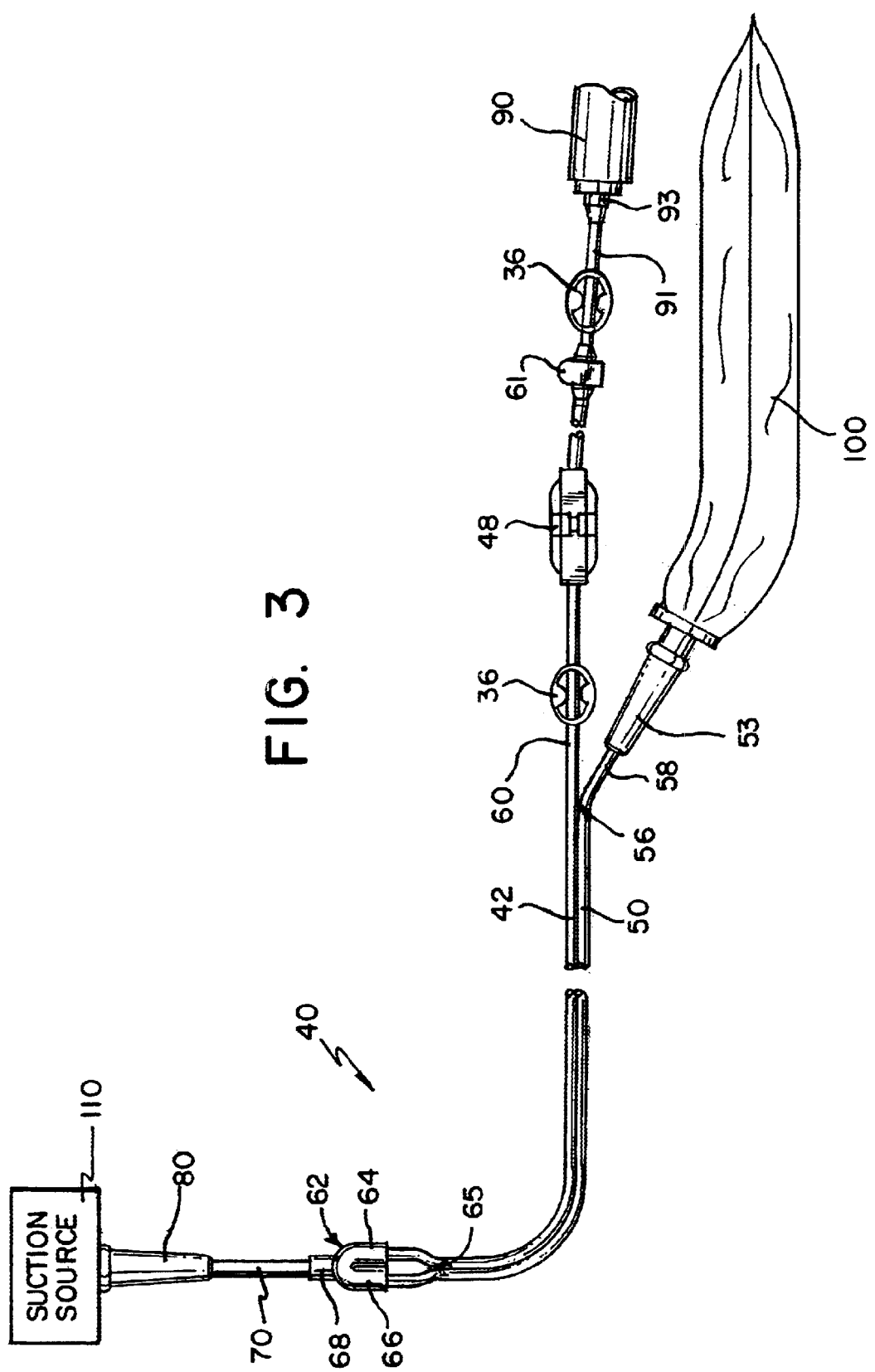
FIG. 3 is a side elevational view of the fluid management assembly of FIG. 2 shown in use with conventional surgical equipment during an operative procedure.

Referring to FIGS. 2 and 3, a fluid management assembly is presented and is generally indicated at 40. FIG. 3 illustrates the fluid management assembly 40 in use according to the present invention with conventional accessory equipment during a typical endoscopic procedure, as will be described in greater detail hereinafter. The fluid management assembly 40 may be referred to as having a dual lumen design and comprises a first fluid carrying member 42 and a second fluid carrying member 50. The first fluid carrying member 42 has a first end 44 and an opposing second end 46. The first end 44 preferably connects to a first connector 48 which is designed to fluidly mate with outflow tubing 91 which includes a connector 93 at one end for mating with an endoscope 90 (e.g., hysteroscope). One type of suitable connector 48 is a large bore Quosina connector which is presented to the sterile field in a capped state. More specifically, the first connector 48 provides fluid communication between an outflow port (not shown) of the hysteroscope 90 and the first fluid carrying member 42 through the outflow tubing 91.

The second fluid carrying member 50 includes a first end 52 and an opposing second end 54 with the second ends 46, 54 of the first and second fluid carrying members 42, 50, respectively, being positioned proximate one another. The first end 52 is coupled to a pouch drape 100 (e.g., hysteroscope pouch drape) by means of a second connector 53 so that fluid communication is provided between the hysteroscope pouch drape 100 and the second fluid carrying member 50 for drainage of fluid build-up within the drape 100 during the surgical procedure. One suitable type of second connector 53 is a suction connector for fluidly connecting the drape 100 to the assembly 40.

In the illustrated embodiment, each of the first and second fluid carrying members 42, 50 comprises a predetermined length of tubing material. The first and second fluid carrying members 42, 50 are preferably co-joined (affixed) along at least a portion of each of their lengths. For the purpose of illustration and according to one exemplary embodiment, the first and second fluid carrying members 42, 50 are co-joined for a length of approximately 10 feet and separate at a first location 56 to form a drape leg 58 and a suction outflow leg 60. It will be appreciated that the drape leg 58 comprises a length of the second fluid carrying member 50 extending from the first location 56 to the first end 52. The suction outflow leg 60 comprises a length of the first fluid carrying member 42 extending from the first location 56 to the first end 44. In the exemplary embodiment, the drape leg 58 has a length of approximately 10 inches and the suction outflow leg 60 has a length of about 20 inches. The suction outflow leg 60 is thus attached to the outflow tubing 91 at the connector 48. The outflow tubing 91 extends from the connector 48 to the endoscope 90 (e.g., hysteroscope) and serves to transfer fluid from the outflow port of the endoscope 90 to the suction outflow leg 60.

In a similar manner, the co-joined first and second fluid carrying members 42, 50 separate at a second location 65 which is distal to the first location 56. The separation at the second location 65 causes the first and second fluid carrying members 42, 50 to be spaced from one another for a predetermined length so that each of the members 42, 50 may be grasped and manipulated as will be described in greater detail hereinafter.

Preferably, the outflow tubing 91 is provided with an atmospheric vent 61 which is disposed proximate to the connector end 93 and thus proximate to the hysteroscope 90. In the exemplary embodiment, the atmospheric vent 61 is formed approximately 6 inches from the outflow connection of the hysteroscope 90 (at the connector end 93). The atmospheric vent 61 permits atmospheric pressure to enter the outflow port of the hysteroscope 90 and this results in a pressure increase at the outflow port. Other features of the atmospheric vent 61 will be described hereinafter when the operation of assembly 40 is described in greater detail.

The fluid management assembly 40 further includes a Y-connector which is generally indicated at 62. The Y-connector 62 is formed of first and second spaced legs 64, 66, respectively, which converge to a main leg 68 which extends in a direction away from the first and second spaced legs 64, 66. The first leg 64 mates with and is secured to the second end 46 of the first fluid carrying member 42 and the second leg 66 mates with and is secured to the second end 54 of the second fluid carrying member 50. Thus, the first leg 64 serves to receive the fluid flowing through the first fluid carrying member 42 from the hysteroscope 90 and the second leg 66 serves to receive the fluid flowing through the second fluid carrying member 50.

The Y-connector 62 acts to mix and direct the fluids from the independent fluid conduits (members 42, 50) to a suction conduit, generally indicated at 70. The main leg 68 of the Y-connector 62 is coupled to the suction conduit 70 so that fluid communication is established therebetween. More specifically, the suction conduit 70 is connected at a first end 72 to the Y-connector 62 and connects at a second end 74 to a suction source 110 by means of an adapter 80 which is designed to provide a secure attachment between the suction source 110 and the assembly 40 and provide fluid communication therebetween. It will be appreciated that the suction source 110 provides a suction force throughout the system and also serves as a collection receptacle for receiving fluids from both the outflow port of the hysteroscope 90 and the hysteroscopy pouch drape 100. In one exemplary embodiment, the suction source 110 comprises a suction cannister and the suction conduit 70 comprises a predetermined length of tubing. A suitable suction cannister 110 is commercially available from a number of manufacturers, including Bemis, Baxter, and Abbott Laboratories. According to one exemplary embodiment of the present invention, the suction conduit 70 has a length of approximately 6 inches.

The fluid management assembly 40 typically will also include the pinch clamp 36 which is disposed about the first fluid carrying member 42 for selectively restricting the flow of fluid within the first fluid carrying member 42. Any number of suitable pinch clamps 36 may be used with assembly 40. The illustrated pinch clamp 36 has a ratchet mechanism that selectively pinches the first fluid carrying member 42. The first fluid carrying member 42 is disposed between the pair of protuberances 38 and as the ratchet mechanism is actuated, the distance between the protuberances 38 either decreases resulting in the first fluid carrying member 42 being increasingly pinched causing an increased restriction in the fluid flow through member 42 or the distance decreases resulting in an increase in fluid flow through the first fluid carrying member 42. In the illustrated embodiment, two pinch clamps 36 are shown, one being disposed about the suction outflow leg 60 and the other disposed about the outflow tubing 91. It will be understood that the precise location of the pinch clamps 36 is not critical and depending upon a number of factors, the pinch clamps 36 may be positioned at a variety of locations along the first fluid carrying member 42.

According to the present invention, it has been discovered that the repositioning of the Y-connector 62 yields several key benefits which result in improved distention of the uterus during the surgical procedure. More specifically, the distance between the Y-connector 62 and the suction source 110 is significantly reduced as it has been discovered that improved performance is realized by relocating the Y-connector 62 to a more proximate position relative to the suction source 110. The assembly 40 according to the present invention provides constant flow to the hysteroscope 90 and to the hysteroscopy pouch drape 100 by elongating the legs of the Y-tubing set in order to minimize mixing and dependency. In other words, the length of each of the drape leg 58 and the suction outflow leg 60 is increased and represent independent fluid conduits which extend separately from the sterile field before combining at the Y-connector 62. By repositioning the Y-connector 62 closer to the suction source 110, the Y-connector 62 and the fluid traveling therethrough are exposed to greater suction forces because the Y-connector 62 is located in a more downstream location relative to the suction source 110 and thus the suction forces acting on the Y-connector 62 are greater and the influence of any variances in fluid between the endoscope line and the drape line are minimized. In the illustrated embodiment, the distance between the Y-connector 62 and the suction source 110 is less than about one foot and preferably is approximately 6 inches. Conventionally, the Y-connector is connected to a conduit (main fluid carrying member 34) having a length of about 108 inches and the fluid was to travel this distance before being deposited into the collecting receptacle (suction canister 110). It will be understood that the aforementioned lengths are merely illustrative and of an exemplary nature and do not limit the scope of the present invention.

Referring now to FIGS. 1–3. Advantageously, the repositioning of the Y-connector 62 in the present assembly 40 eliminates the disadvantages which were associated with fluid pooling within the Y-connector 18 of the conventional assembly 10. In the conventional assembly 10, the Y-connector 18 drapes downwardly from the hysteroscopy pouch drape and the hysteroscope and ultimately becomes saturated with fluid as the fluid collects or pools in the Y-connector 18 as the fluid flows downwardly into the Y-connector 18. In such an assembly 10 which is open to atmosphere, the fluid wants to seek its own level and hence the fluid collected in the hysteroscope pouch drape wants to flow upwardly into the leg of tubing which leads to the hysteroscope. This reflux action prevents fluid from exiting the outflow port of the hysteroscope and hence inhibits fluid turnover in the uterus.

By positioning the Y-connector 62 in a more downstream location closer to the suction source 110 itself, the pooling of fluid within the Y-connector body is eliminated since the fluid is entrained upwardly into the Y-connector 62. More specifically, the suction source 110 is positioned at least above the level of the first and second fluid carrying members 42, 50, respectively, and also preferably above the level of the pouch drape 100. This results in the fluid being entrained upwardly into the Y-connector 62 during operation. This is in contrast to the previous assembly 10 in which the fluid is entrained downwardly into the Y-connector and thus tends to pool therein resulting in a liquid seal being formed. As previously described, the presence of a liquid seal results in sumping action. The Y-connector leg, having the lesser resistance, is effectively sealed which results in cycling of intrauterine pressures, uterine bleeding and an overall increase in the surgical procedure time. By virtue of repositioning of the Y-connector 62 in the present assembly 40, the first and second legs 64, 66 of the Y-connector 62 are exposed to lower negative pressures and, in combination with the fact that the Y-connector 62 is exposed to greater suction forces due to its repositioning, the overall performance of the assembly 40 is significantly increased in comparison to the prior mechanical restrictor assembly 10.

The assembly 40 has an anti-siphon conduit arrangement provided for use on the outflow port of the hysteroscope 90. This arrangement relieves negative pressures associated with the vertical positioning of the outflow conduit member (first fluid carrying member 42) relative to the uterus. The present assembly 40 also reduces negative pressure applied to uterus when suction is attached directly to the outflow port of the hysteroscope 90. Furthermore, the atmospheric vent 61 provided in the outflow tubing 91 (scope line) provides suction relief during the surgical procedure.

By increasing the length of the drape leg 58 and the suction outflow leg 60 and maintaining the same or similar inner diameters thereof, the flow/pressure within each leg 58, 60 is essentially the same; however, the first and second fluid carrying members 42, 50 engage the Y-connector 62 further downstream where the suction forces are greater. The inverted positioning of the Y-connector 62 in this downstream location results in the resistance from the fluid in either leg 58, 60 being minimized. Because of the substantial length of the drape and suction outflow legs 58, 60 prior to their connection to the Y-connector 62, it is not necessary to restrict flow in the second fluid carrying member 50 (drape line) to provide adequate suction on the hysteroscope 90 when the drape 100 is empty. In one exemplary embodiment, the inner diameter of the suction outflow leg 60 is about 0.190 inches and the inner diameter of the drape leg 58 is 0.125 inches.

Thus, the present invention eliminates the need for using a flow restrictor with the endoscopic line and this generally reduces the cost of the surgical procedure and the complexity thereof. Furthermore, the accumulated fluid collected within the drape 100 is unlikely to create a fluid seal which would restrict flow from the hysteroscope 90 when the present assembly 40 is used. Accordingly, pressure fluctuations in the uterus are eliminated and flow is enhanced when fluid is aspirated simultaneously from the drape 100 and the hysteroscope 90. Using the dual lumen suction design of the present assembly 40 of the present invention, the pressure inside of the uterus is not changed based upon the method of fluid outflow. In other words, the pressure does not change whether the fluid flows by gravity or by means of suction assist. Furthermore, the pressure inside of the uterus is not affected by the presence of fluid in the drape 100 during suction assisted outflow of the fluid.

Another consideration in optimizing the level of distention is the rate of which the fluid is being pulled from the uterus. The fluid flow rate is important for visualization purposes (i.e. to minimize white and red outs). This fluid flow rate is a function of airflow rate at the first end of the endoscopic line that is connected to the outflow port of the endoscope. The dual lumen design of the present invention yields equal airflow rates at the points of connection between the endoscopic line and the outflow port of the endoscope 90 and the drape line and the drape 100 and the present design further eliminates the fluctuation of airflow through the endoscopic line when fluid is present in the drape 100. The airflow rate through the endoscopic line is not reduced when fluid is present in the drape. This results in improved pressure balance and thus distention and visualization are likewise improved.

Another advantage of the present invention is that the use of co-joined tubing in the assembly 40 gives the surgeon flexibility in selecting the length for the drape and suction outflow legs 58, 60. This permits the surgeon to custom tailor the length of either of legs 58, 60. For example, if the surgeon prefers to increase the length of the suction outflow leg 60, the surgeon may simply pull the legs 58, 60 apart from one another to further separate the two from one another and thereby increase the length of the leg portions 58, 60. This permits the surgeon greater latitude in using the assembly 40 with a number of types of medical equipment and the precise location of the equipment is not critical since the length of the leg portions 58, 60 may be customized to permit the assembly 40 to be effectively hooked-up to all of the requisite equipment.

While the invention has been particularly shown and described with reference to the preferred embodiments thereof, it will be understood by those skilled in the art that various changes in form and detail may be made therein without departing from the spirit and scope of the invention.

What is claimed is:

1. A fluid management assembly for use in an endoscopic procedure, the assembly comprising:

a first line defining a passage for the flow of fluid and having a length, the first line having a first end for connection to an endoscope and an opposing second end;

a second line defining a passage for the flow of fluid and having a length, the second line having a first end for connection to a drape and an opposing second end;

a Y-connector having first and second legs in fluid communication with the second ends of the first and second lines, and a third line coupled at a first end to a third leg of the Y-connector, the third line having a second end for connection to a suction source, the third line having a predetermined length such that the Y-connector is positioned in close proximate relation to the suction source, the length of the third line being less than the length of each of the first and second lines.

2. An assembly according to claim 1, wherein the first and second lines are affixed along a portion of the length of each of the first and second lines.

3. An assembly according to claim 1, wherein the first, second, and third lines are formed of a tubing material.

4. An assembly according to claim 1, wherein the first line has a first inner diameter and the second line has a second inner diameter, the first inner diameter being the same or greater than the second inner diameter.

5. An assembly according to claim 1, wherein the first and second lines are affixed along a first portion of the lengths thereof, the first and second lines being separated from one another at a first location and a second location.

6. An assembly according to claim 5, wherein a portion of the first line from the first location to the first end defines a scope leg and a portion of the second line from the first location to the first end defines a drape leg.

7. An assembly according to claim 6, wherein the scope leg is longer than the drape leg.

8. An assembly according to claim 1, wherein the third line has a length of about 6 inches.

9. An assembly according to claim 1, wherein the lengths of the first and second lines are greater than about 10 feet.

10. An assembly according to claim 1, wherein the length of the third line is at most one foot and wherein the lengths of the first and second lines are at least about 7 feet, whereby pressure within the second and third lines is substantially equal.

11. An assembly according to claim 1, wherein the Y-connector commingles the fluids from the first and second lines for delivery to the third line through the third leg, the commingling being at a distance of less than one foot from the suction source.

12. An assembly according to claim 1, wherein the first and second legs of the Y-connector are positioned relative to the first and second lines such that the fluids flowing therethrough are entrained upwardly into the Y-connector.

13. An assembly according to claim 1, wherein the first line includes an atmospheric vent for permitting atmospheric pressure to enter the first line for increasing the pressure at an outflow portion of the endoscope.

14. An endoscopic fluid management system comprising:
a drape for collecting a first fluid;
an endoscope for fluidly irrigating an operative area with a second fluid;
a suction source for applying a suction force and collecting the first and second fluids after the first fluid has been collected in the drape and the second fluid has irrigated the operative site; and
a fluid management assembly including:
a first line defining a passage for the flow of the second fluid, the first line having a first end connected to the endoscope and an opposing second end;
a second line defining a passage for the flow of the first fluid, the second line having a first end connected to the drape and an opposing second end;
a Y-connector having a first leg in fluid communication with the second end of the first line and a second leg in fluid communication with the second end of the second line; and
a third line coupled at a first end to a third leg of the Y-connector and connected at a second end to the suction source, wherein the third line has a predetermined length such that the Y-connector is positioned in close proximate relation to the suction source, the length of third line being less than a length of each of the first and second lines.

15. A system according to claim 14, wherein the third line extends upwardly from the Y-connector to the suction source due to the Y-connector being positioned in close proximate relation to the suction source.

16. A system according to claim 14, wherein the first and second legs of the Y-connector are positioned relative to the first and second lines such that the fluids flowing therethrough are entrained upwardly into the Y-connector resulting in the elimination of pooling in the Y-connector.

17. A system according to claim 14, wherein the first, second, and third lines are formed of tubing material.

18. A system according to claim 14, wherein the first and second lines are affixed along a first portion of the lengths thereof, the first and second lines being separated from one another along a second portion and a third portion.

19. A system according to claim 17, wherein a length of the first line from the first point to the first end comprises a scope leg and a length of the second line from the first point to the first end comprises a drape leg, the length of the scope leg being about 20 inches and the length of the drape leg being about 10 inches.

20. A system according to claim 14, wherein the first and second lines are connected to the Y-connector so that the fluid is entrained upwardly into the Y-connector and the length of the first and second lines is such that the pressure within each of these lines is substantially equal.

* * * * *